(12) United States Patent
Anderson (10) Patent No.: US 9,421,361 B2
(45) Date of Patent: Aug. 23, 2016

(54) METHODS FOR FABRICATING STIMULATOR LEADS

(71) Applicant: BOSTON SCIENTIFIC NEUROMODULATION CORPORATION, Valencia, CA (US)

(72) Inventor: Meredith L. Anderson, Billerica, MA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 85 days.

(21) Appl. No.: 14/204,233

(22) Filed: Mar. 11, 2014

(65) Prior Publication Data

US 2014/0190009 A1 Jul. 10, 2014

Related U.S. Application Data (63) Continuation of application No. 11/319,291, filed on Dec. 27, 2005, now Pat. No. 8,700,178.

(51) Int. Cl.
*H01K 3/22* (2006.01)
*A61N 1/05* (2006.01)

(52) U.S. Cl.
CPC ............... *A61N 1/05* (2013.01); *A61N 1/0551* (2013.01); *A61N 1/0553* (2013.01); *A61N 1/0529* (2013.01); *Y10T 29/4921* (2015.01); *Y10T 29/4922* (2015.01)

(58) Field of Classification Search
CPC ............. A61N 1/0551; A61N 1/0529; A61N 1/0534; A61N 1/0553; A61N 1/36017; H01L 23/4985; H05K 1/118; Y10T 29/49158; Y10T 29/49155; Y10T 29/49224; Y10T 29/49117; Y10T 29/4922; Y10T 29/4921

USPC ........ 29/848, 831, 832, 837, 842, 852, 877, 29/883, 885; 607/36, 37, 53, 54, 116
See application file for complete search history.

(56) References Cited

U.S. PATENT DOCUMENTS 3,623,479 A  11/1971  Day
3,718,142 A  2/1973  Mulier
(Continued)

FOREIGN PATENT DOCUMENTS

EP  1424097 A1  6/2004
JP  H02-128773 A  5/1990
(Continued)

OTHER PUBLICATIONS

Deman, P. R., et al., "Design, Construction, and Mechanical Optimisation Process of Electrode with Radial Current Flow in the Scala Tympani." Journal of Neuroscience Methods. vol. 28, pp. 143-150 (2003).

(Continued)

*Primary Examiner* — Thiem Phan
(74) *Attorney, Agent, or Firm* — Lowe Graham Jones PLLC; Bruce E. Black (57) ABSTRACT

A lead for a stimulation device can include an array of electrodes with each electrode having a front surface and a back surface; a plurality of conductors; a carrier formed around the array of electrodes; and a biocompatible material that may be disposed over and/or joined with the carrier and the back surfaces of the electrodes. A conductor is attached to the back surface of each electrode. The carrier can be formed around the array of electrodes, but does not completely cover the front surface or back surface of the electrodes.

20 Claims, 5 Drawing Sheets

(56) References Cited

U.S. PATENT DOCUMENTS

| | | |
|---|---|---|
| 3,724,467 A | 4/1973 | Avery et al. |
| 4,286,249 A | 8/1981 | Lewis et al. |
| 4,628,937 A | 12/1986 | Hess et al. |
| 4,660,571 A | 4/1987 | Hess et al. |
| 4,686,765 A | 8/1987 | Byers et al. |
| 4,774,952 A | 10/1988 | Smits |
| 4,907,601 A | 3/1990 | Frick |
| 4,969,463 A | 11/1990 | Dahl et al. |
| 5,193,539 A | 3/1993 | Schulman et al. |
| 5,193,540 A | 3/1993 | Schulman et al. |
| 5,312,439 A | 5/1994 | Loeb |
| 5,417,719 A | 5/1995 | Hull et al. |
| 5,458,124 A | 10/1995 | Stanko et al. |
| 5,817,030 A | 10/1998 | Tarjan et al. |
| 5,897,583 A | 4/1999 | Meyer et al. |
| 6,038,484 A | 3/2000 | Kuzma |
| 6,051,017 A | 4/2000 | Loeb et al. |
| 6,052,608 A | 4/2000 | Young et al. |
| 6,152,882 A | 11/2000 | Prutchi |
| 6,181,969 B1 | 1/2001 | Gord |
| 6,343,226 B1 | 1/2002 | Sunde et al. |
| 6,516,227 B1 | 2/2003 | Meadows et al. |
| 6,604,283 B1 | 8/2003 | Kuzma |
| 6,609,029 B1 | 8/2003 | Mann et al. |
| 6,609,032 B1 | 8/2003 | Woods et al. |
| 6,741,892 B1 | 5/2004 | Meadows et al. |
| 6,757,970 B1 | 7/2004 | Kuzma et al. |
| 6,961,622 B2 | 11/2005 | Gilbert |
| 7,006,859 B1 | 2/2006 | Osorio et al. |
| 7,010,356 B2 | 3/2006 | Jog et al. |
| 7,146,217 B2 | 12/2006 | Firlik et al. |
| 7,146,221 B2 * | 12/2006 | Krulevitch et al. .......... 607/116 |
| 7,149,586 B2 | 12/2006 | Greenberg et al. |
| 7,221,981 B2 | 5/2007 | Gliner |
| 7,244,150 B1 | 7/2007 | Brase et al. |
| 7,305,268 B2 | 12/2007 | Gliner et al. |
| 7,761,165 B1 | 7/2010 | He et al. |
| 2001/0029395 A1 | 10/2001 | Stewart et al. |
| 2002/0128700 A1 | 9/2002 | Cross |
| 2003/0187490 A1 | 10/2003 | Gliner |
| 2003/0204228 A1 | 10/2003 | Cross et al. |
| 2004/0015221 A1 | 1/2004 | Kuzma |
| 2004/0043052 A1 | 3/2004 | Hunter et al. |
| 2004/0054366 A1 | 3/2004 | Davison et al. |
| 2004/0059392 A1 | 3/2004 | Parramon et al. |
| 2004/0098074 A1 | 5/2004 | Erickson et al. |
| 2005/0004638 A1 | 1/2005 | Cross |
| 2010/0152818 A1 | 6/2010 | Anderson et al. |

FOREIGN PATENT DOCUMENTS

| | | |
|---|---|---|
| WO | WO-9837926 A1 | 9/1998 |
| WO | WO-9843700 A1 | 10/1998 |
| WO | WO-9843701 A1 | 10/1998 |
| WO | WO-0117315 A1 | 3/2001 |
| WO | 03/026739 A2 | 4/2003 |

OTHER PUBLICATIONS

International Application No. PCT/US07/60310, International Search Report and Written Opinion mailed Aug. 27, 2008.
European Search Report for European Patent Application No. 07753626.0 mailed Apr. 18, 2011.
U.S. Appl. No. 11/319,291, Appeal Brief filed Oct. 10, 2013.
U.S. Appl. No. 11/319,291, Official Communication mailed Apr. 22, 2013.
U.S. Appl. No. 11/319,291, Official Communication mailed Aug. 13, 2013.
U.S. Appl. No. 11/319,291, Official Communication mailed Aug. 4, 2008.
U.S. Appl. No. 11/319,291, Official Communication mailed Dec. 24, 2008.
U.S. Appl. No. 11/319,291, Official Communication mailed Jun. 20, 2011.
U.S. Appl. No. 11/319,291, Official Communication mailed Jun. 23, 2010.
U.S. Appl. No. 11/319,291, Official Communication mailed Mar. 19, 2009.
U.S. Appl. No. 11/319,291, Official Communication mailed Nov. 9, 2011.
U.S. Appl. No. 11/396,309, Official Communication mailed Aug. 20, 2008.
U.S. Appl. No. 11/396,309, Official Communication mailed Jan. 26, 2009.
U.S. Appl. No. 11/396,309, Official Communication mailed Jun. 10, 2009.
U.S. Appl. No. 12/712,107 Official Communication mailed Aug. 14, 2012.
U.S. Appl. No. 12/712,107 Official Communication mailed Mar. 15, 2012.
U.S. Appl. No. 12/712,107 Official Communication mailed Sep. 3, 2013.

* cited by examiner

METHODS FOR FABRICATING STIMULATOR LEADS

CROSS-REFERENCE TO RELATED APPLICATIONS

This patent application is a continuation of U.S. patent application Ser. No. 11/319,291, filed on Dec. 27, 2005, now allowed, which is incorporated herein by reference.

FIELD OF THE INVENTION

The invention is directed to stimulators and stimulator components and methods of making the devices. The invention is also directed to stimulators and stimulator components with electrodes located in a carrier, as well as methods of making the devices.

BACKGROUND OF THE INVENTION

Stimulators have been developed to provide therapy for a variety of disorders, as well as for other treatments. For example, stimulators can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

As one example, spinal cord stimulation is a well accepted clinical method for reducing pain in certain populations of patients. Stimulators have been developed to provide therapy for a variety of treatments. For example, stimulators can be used to stimulate nerves, such as the spinal cord, muscles, or other tissue. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue. As an example, electrical pulses can be provided to the dorsal column fibers within the spinal cord to provide spinal cord stimulation.

BRIEF SUMMARY OF THE INVENTION

In one embodiment, a method of making a lead for a stimulation device includes forming an array of electrodes in a pre-determined arrangement. A carrier is formed around the array of electrodes to maintain the arrangement. A biocompatible material is disposed over at least a portion of the carrier to form an array body that includes the array, the carrier, and the biocompatible material.

In another embodiment, a lead for a stimulation device includes an array of electrodes; a plurality of conductors; a carrier formed around the array of electrodes; and a biocompatible material disposed over, and in contact with, the carrier and the back surfaces of the electrodes. The electrodes have a front surface and a back surface, and a conductor is attached to the back surface of each electrode. The carrier is formed around the array of electrodes, but does not completely cover the front surface or back surface of the electrodes. The biocompatible material and the carrier may be different, e.g., of different materials or the same material but having different durometers (hardness) or they may be exactly the same material but joined together during the manufacturing process.

In another embodiment of the invention, a system for stimulation includes an electronic subassembly, a lead, and a plurality of conductors. The lead includes an array of electrodes with each electrode having a front surface and a back surface; a carrier formed around the array of electrodes but not completely covering the front surface or back surface of the electrodes; and a biocompatible material disposed over, and in contact with, the carrier and the back surface of the electrodes. The carrier and the biocompatible material are different. The conductors are attached to the back surface of each electrode and couple the electrodes to the electronic subassembly.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION OF THE INVENTION

The invention is directed to stimulators and stimulator components and methods of making the devices. The invention is also directed to stimulators and stimulator components with electrodes located in a carrier, as well as methods of making the devices.

Examples of stimulators are found in U.S. Pat. Nos. 6,181,969; 6,516,227; 6,609,029; 6,609,032; and 6,741,892; and U.S. patent application Ser. No. 11/238,240, all of which are incorporated by reference.

In some designs of stimulators, electrodes are presented on a lead. Examples of leads include, for example, percutaneous leads and paddle leads. It is generally desirable that the electrode (or electrode contacts) of such stimulators are reproducibly located on the lead, with surface areas exposed to the tissue to be stimulated. Making such leads may become difficult when the electrodes are small and/or a large number of electrodes are needed. A reliable method of holding the electrodes in the desired position during the process of forming the lead is desirable.

In at least some applications, it is desirable that the electrode(s) of a stimulator be located and secured in position during the process of manufacturing the stimulator. Methods of locating and securing the position of the electrode(s) during the manufacturing process have been described, for example, in U.S. Pat. No. 6,757,970, which is herein incorporated by reference. One conventional method of positioning electrodes during the manufacturing process involves using a metal foil carrier or stamped iron plate as a temporary carrier to which the electrodes are affixed during the process of forming the lead. The temporary carrier is then typically removed using an etching process. Such a method of using a temporary metal foil that is later etched away to make an electrode array is described in U.S. Pat. No. 6,038,484.

The etching process often involves chemical etching, and in at least some instances an acid mixture. The process of chemical etching may result in a longer manufacturing cycle time, as it includes a post-etching soaking and drying treatment. Use of an acid mixture may also pose safety hazards during the manufacturing process. Fumes from the acid mixture may also discolor elements of the lead, such as polyurethane tubing.

In at least some applications, it is desirable to manufacture a lead for a stimulator that does not include removal of a temporary carrier that positions electrodes during the manufacturing process. In some instances, such a manufacturing method may result in savings of time, money, or operator oversight. For example, a method of making a lead can include positioning electrodes in a carrier that becomes part of the final product, thereby avoiding a process for removing a temporary carrier.

Figure 10:
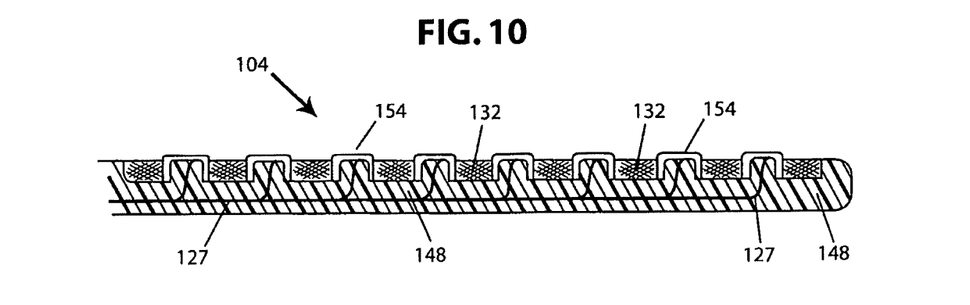
FIG. 10 is a schematic cross-sectional view of the array body of FIG. 9 at line 10-10.

Referring to FIG. 10, one example of a method of making a lead for a stimulation device includes forming an array of electrodes 154 in a pre-determined arrangement, forming a carrier 132 around the array, and placing a biocompatible material 148 over at least a portion of the carrier 132. In this method, an array of electrodes 154 is formed in a pre-determined arrangement in an array body 104. The electrodes 154 can be made using any conductive material. Examples of suitable materials include, for example, metals, alloys, conductive polymers, and conductive carbon. The number of electrodes 154 in the array of electrodes 154 may vary, depending on the application for which the electrodes 154 will be used (e.g., brain stimulation, neural stimulation, spinal cord stimulation, etc.). For example, there can be two, four, six, eight, ten, twelve, fourteen, sixteen, or more electrodes 154. As will be recognized, other numbers of electrodes 154 may also be used.

The arrangement of the electrode(s) 154 may vary. For example, the electrodes 154 may be arranged in a paddle type array, in which the electrodes are arranged in two or more parallel columns, as illustrated schematically in FIGS. 5, 6, 8 and 9. The columns of electrodes can be aligned or staggered from one another, or in any other desired column or row arrangement. The electrodes may also be arranged, for example, in a row, or "in line," along the longitudinal axis of a small diameter lead body. Optionally, the electrodes may be placed linearly, circularly, or elliptically. The arrangement of electrodes may be symmetrical or asymmetrical. As will be recognized, other arrangements of electrodes are also possible.

Figure 2:
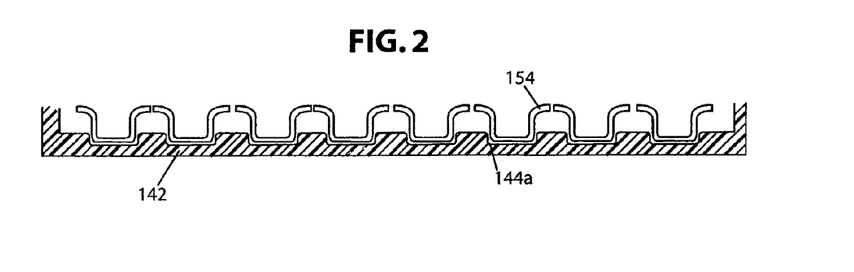
FIG. 2 is a schematic cross-sectional view of the array of electrodes positioned within the carrier mold of FIG. 1.

In one embodiment, the electrodes 154 are placed in the desired array arrangement by positioning the electrodes in a carrier mold 142 as illustrated schematically in FIG. 2. Suitable materials for the carrier mold 142 include, but are not limited to, metal, wax, wood, polymers (including plastics), paper, composite materials, and the like. Preferably, the carrier mold 142 is made of a durable material that allows the carrier mold 142 to be reused.

In one embodiment, the carrier mold 142 includes electrode positioning features 144a, e.g., indentations or depressions in the carrier mold 142, that are disposed in the desired array arrangement. The electrode positioning features 144a aid positioning of the electrodes 154 in the pre-determined arrangement. For example, the electrodes 154 may be placed in a carrier mold 142 that has indentations in the bottom of the mold that accommodate the shape of the electrodes 154 and keep the electrodes 154 in position during the process of manufacturing the carrier 132. For example, the electrodes 154 may be concave and the carrier mold 142 may have indentations that accommodate the concave shape of the electrodes 154. Preferably, at least a portion of the side surface of the electrodes 154 remains exposed within the carrier mold 142.

Electrode positioning features 144a can also include, for example, depressions, protrusions, extensions or any other feature that aids positioning of the electrodes 154. For example, the carrier mold 142 may have protrusions from the bottom of the mold upon which a concave electrode surface can sit. Optionally, the position of the electrodes 154 in the carrier mold 142 may be further secured using a vacuum table.

Figure 3:
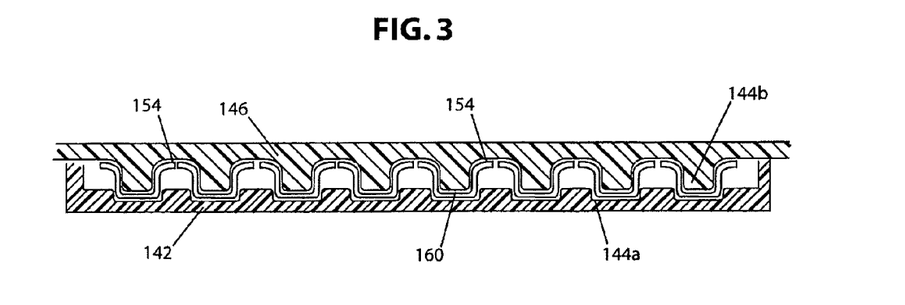
FIG. 3 is a schematic cross-sectional view of one embodiment of an array of electrodes positioned within a carrier mold and having a carrier mold cover over the carrier mold, according to the invention.

After the electrodes 154 are positioned in the carrier mold 142, a carrier mold cover 146 is placed over the electrodes 154 and the carrier mold 142. FIG. 3 illustrates schematically a cross-sectional view of one embodiment of an array of electrodes 154 positioned within a carrier mold 142 with a carrier mold cover 146. Suitable materials for the carrier mold cover 146 include, but are not limited to, metal, wax, wood, polymers (including plastics), paper, composite materials, and the like. Preferably, the carrier mold cover 146 is made of a durable material that allows the carrier mold cover 146 to be reused. It will be recognized that the array of electrodes 154 may be formed in a pre-determined arrangement either before or during the process of forming a carrier 132 around the array of electrodes 154.

In one embodiment, the carrier mold cover 146 also has electrode positioning features 144b. As illustrated in FIG. 3, in one embodiment, the carrier mold cover 146 has electrode positioning features 144b that are protrusions that fit within a portion of the electrode 154. The electrode positioning features 144b could also be depressions. Optionally, the carrier mold cover 146 protects at least one surface of the electrode 154 from coverage by a carrier material during the process of forming the carrier 132 (FIG. 4) around the array of electrodes 154. For example, the carrier mold cover 146 may be designed such that it prevents or reduces contact or coverage of at least one surface 160 of the electrode 154 with the carrier material during the process of forming the carrier around the electrodes 154 (FIG. 3). The protected portion of the surface 160 of the electrode 154 may be used, for example, to connect to components of the electrical circuitry. In one embodiment, a carrier mold cover 146 that prevents or reduces contact of one surface 160 of the electrode 154 with the carrier material is illustrated schematically in FIGS. 3 and 4. In other embodiments, only one of the carrier mold 142 and carrier mold cover 146 includes electrode positioning features 144b.

Figure 4:
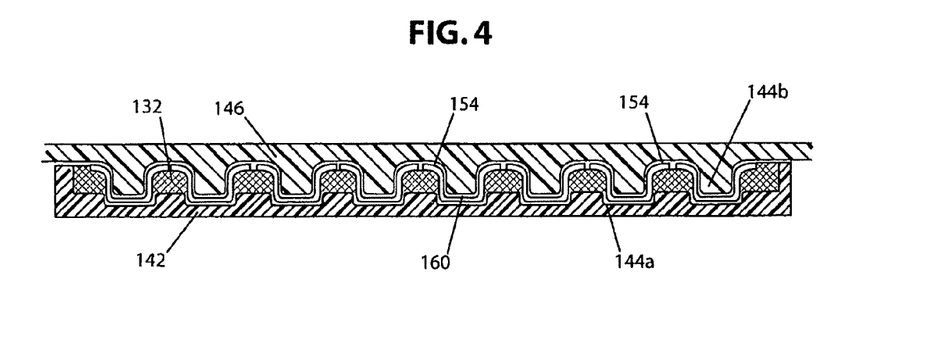
FIG. 4 is a schematic cross-sectional view of one embodiment of an array of electrodes positioned within a carrier mold, with a carrier mold cover over the carrier mold and a carrier molded around the array of electrodes, according to the invention.

The carrier 132 is then formed around the array of electrodes 154 as illustrated in FIG. 4. The carrier 132 can be made of any biocompatible material including, for example, silicone, polyurethane, polyetheretherketone (PEEK), epoxy, and the like.

The carrier 132 may be formed by any process including, for example, molding (including injection molding), casting, and the like. In one embodiment, the carrier 132 is formed by injection molding. Preferably, when forming the carrier, the material of the carrier does not cover the top surface 156, shown in FIG. 5, (or at least a substantial portion of the top surface 156) of the electrodes 154. Also, preferably, the carrier material does not cover the bottom surface 158, shown in FIG. 6, (or at least a substantial portion of the bottom surface 158) of the electrodes 154.

Figure 1:
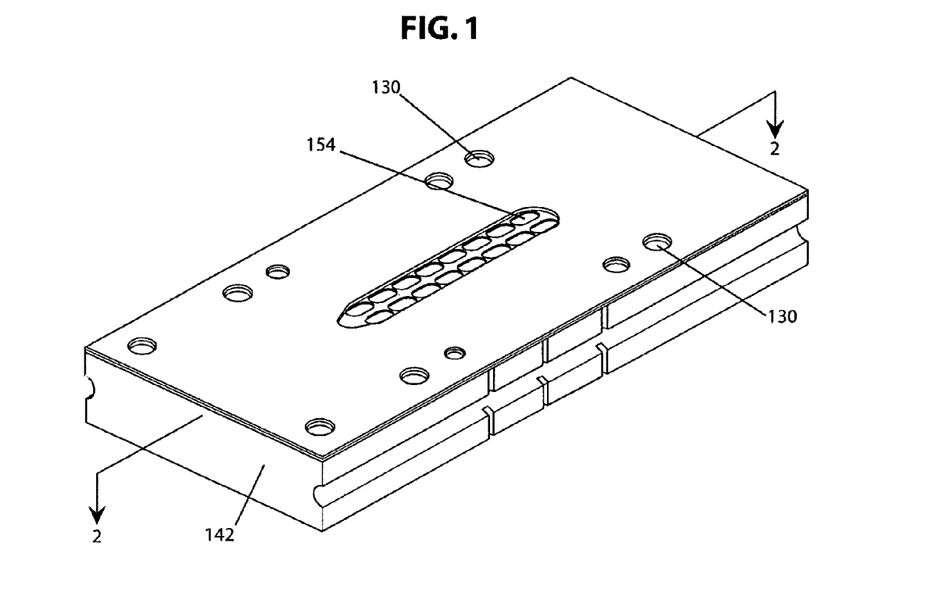
FIG. 1 is a schematic perspective view of one embodiment of an array of electrodes positioned within a carrier mold, according to the invention.

In one embodiment, the carrier mold 142 and carrier mold cover 146 include one or more cooperating locating features 130 (FIG. 1) that aid proper alignment of the carrier mold 142 and carrier mold cover 146. For example, corresponding locating features may be a locating pin inserted into a corresponding hole in a carrier mold 142. A locating pin may be inserted through two halves of a carrier mold to keep the two halves aligned and held together.

Figure 5:
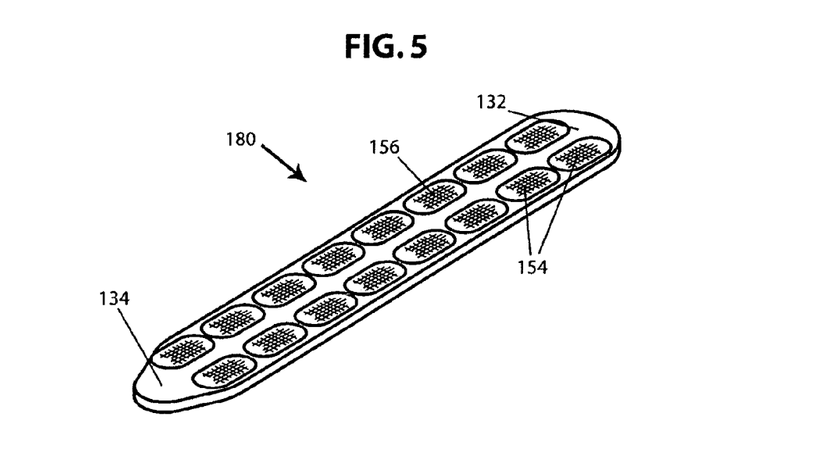
FIG. 5 is a schematic perspective view of one embodiment of the top portion of an array of electrodes with a carrier formed around the array, according to the invention.
Figure 6:
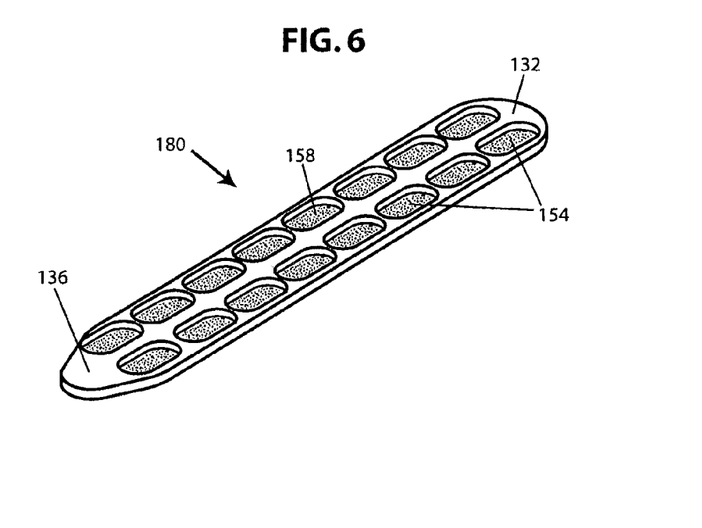
FIG. 6 is a schematic perspective view of one embodiment of the bottom portion of the array of electrodes of FIG. 5, according to the invention.

A top view of the intermediate assembly 180, which includes the completed carrier 132 and the array of electrodes 154, is illustrated schematically in FIG. 5. A bottom view of the intermediate assembly 180, including the carrier 132 and array of electrodes 154, is illustrated schematically in FIG. 6. The carrier 132 may have any shape. Preferably, the carrier 132 is formed around the array of electrodes 154 so that at least one surface, and more preferably both the top and bottom surfaces, of each electrode 154 in the array is exposed. The carrier is typically sufficiently sturdy to maintain the arrangement of the electrodes 154 during the remaining manufacturing steps.

After the carrier 132 is molded around the electrodes 154, conductors 127 are joined to the electrodes 154 positioned in the carrier 132. Optionally, the intermediate assembly 180, which includes the completed carrier 132 and the array of electrodes 154, can be removed from the carrier mold 142 before the conductors 127 are coupled to the electrodes 154. The carrier mold 142 may have a removable top plate that aids in removing the intermediate assembly 180 from the carrier mold 142.

Figure 7:
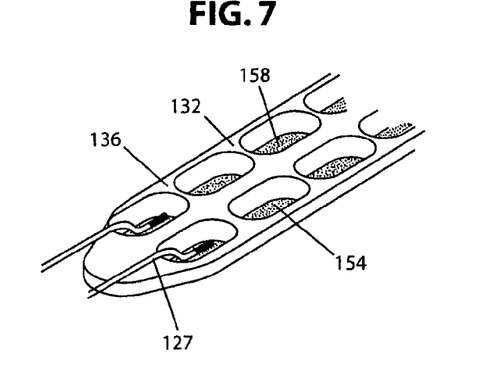
FIG. 7 is a close-up schematic perspective view of the bottom portion of the array of electrodes of FIG. 6, according to the invention.
Figure 8:
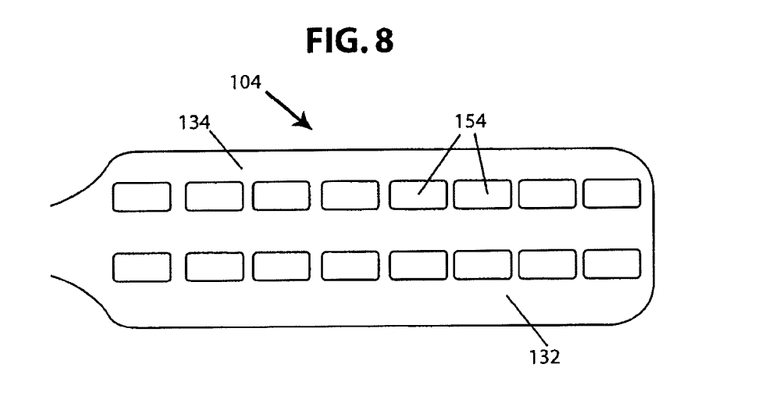
FIG. 8 is a schematic perspective view of one embodiment of the top of an array body comprising an array of electrodes, a carrier formed around the array, and a biocompatible material, where the biocompatible material does not increase the width of the array body as compared to the width of the carrier.
Figure 9:
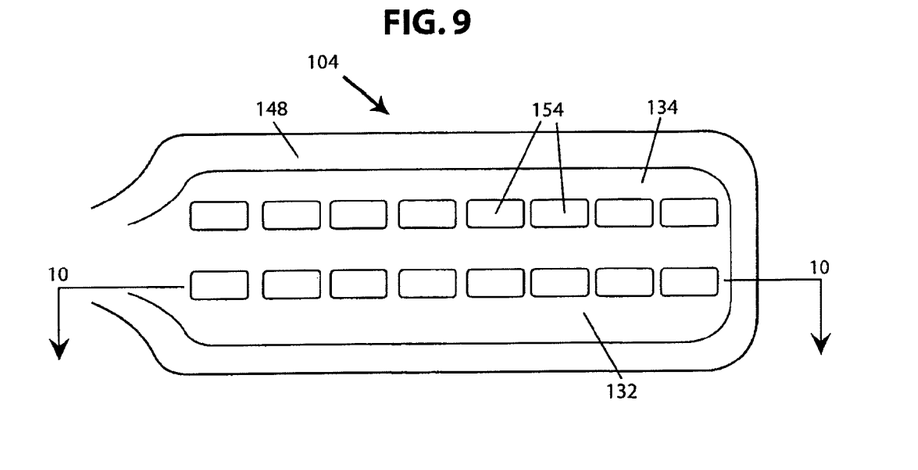
FIG. 9 is a schematic perspective view of one embodiment of the top of an array body comprising an array of electrodes, a carrier formed around the array, and a biocompatible material, where the biocompatible material increases the width of the array body as compared to the width of the carrier.

In one embodiment, the conductors 127 are attached to the electrodes 154 as illustrated in FIG. 7. Preferably, conductors 127 are attached to the back side of the electrodes 154, which is the side of the electrode 154 opposite the side that will be exposed to the body tissue. In another embodiment, the conductors 127 may be joined to the electrodes 154 prior to forming the carrier 132.

Optionally, the exposed surfaces (particularly the bottom surface 158) of the electrode(s) 154 may be cleaned after the carrier is formed around the electrodes 154, but before the conductor(s) 127 are coupled to the electrode(s) 154. The electrode surfaces may be cleaned by any method including, for example, plasma etching, use of a solvent (e.g., alcohols, organic solvents, etc.), and the like.

The conductors 127 can be made of any conductive material. Examples of suitable material for conductors 127 include, for example, metals, alloys, conductive polymers, and conductive carbon. In one embodiment, the conductors 127 are insulated by an insulating material except where the conductor 127 makes contact with the electrode 154. The insulating material may be any material that is a poor conductor of an electrical signal, including, for example, Teflon™, non-conductive polymers, nylon, Mylar, and composite materials. The conductors 127 may be attached to the electrodes by any method including, for example, resistance welding, laser welding, conductive epoxy, and the like. Preferably, the conductors 127 are attached to the electrodes 154 by a method that results in a durable attachment of the conductors 127 to the electrodes 154 under expected usage conditions. The conductor 127 typically traverses the lead to its proximal end to couple the electrodes 154 to a pulse generator (optionally, via other conductive contacts).

Optionally, after the conductors 127 are attached to the electrodes 154, an adhesive may be applied over at least a portion of the conductors 127 and the electrodes 154. Suitable adhesives include, for example, silicones, epoxies, and acrylics. The adhesive may be applied using any method that results in adhesive being applied to the surface of the conductors and/or electrodes including, for example, spray coating, brush coating, dip coating, and the like. In one embodiment, the adhesive applied to the conductors 127 provides stress relief to the conductor/electrode attachment.

In one embodiment, after the conductors 127 are attached to the electrodes 154, but before the biocompatible material 148 is disposed on the carrier 132, a path for the conductors 127 along the carrier 132 is determined and the conductors 127 are optionally secured in position. The conductors 127 may be secured, for example, by an adhesive or by applying tension to another end of the conductor 127. Suitable materials for the adhesive include, for example, silicones, epoxies, acrylics, and the like.

A biocompatible material 148 is then disposed over at least a portion of the carrier 132. The biocompatible material 148 may be disposed over a portion of the carrier 132 by any method including, for example, spray coating, brush coating, molding, and the like.

In one embodiment, the biocompatible material 148 is disposed over a portion of the carrier 132 by a molding process. The carrier 132 and an array of electrodes 154 are placed face down into a mold (i.e., with the top portion 134 of the intermediate assembly 180 down; with the surface of the electrodes 154 that will be exposed to the tissue facing down). Optionally, the mold has a shape that is complementary to the shape of the carrier 132. A cover is placed over the mold and the biocompatible material 148 is added to the mold over the carrier 132. The biocompatible material 148 may be introduced to the mold by any method including, for example, by injection. The biocompatible material 148 is then allowed to harden, cure, or otherwise solidify.

Typically, the biocompatible material 148 covers the back surface 136 of the carrier 132 and increases the thickness of the array body 104, as illustrated in FIG. 10. The biocompatible material 148 typically covers the back surface 158 of the electrodes 154 and the conductors 127 to form an insulating covering over the electrode/conductor connections. In some embodiments, the biocompatible material 148 is disposed on the carrier 132 such that the completed array body 104 has a width greater than the width of the carrier 132 as, for example, illustrated schematically in FIG. 9. Alternatively, the biocompatible material 148 may be disposed on the carrier 132 such that the lead has a width equal to the width of the carrier 132 as, for example, illustrated schematically in FIG. 8.

The top surface 156 of the electrode(s) 154 may or may not extend above the surface of the array body 104. For example, the top surface 156 of the electrode(s) 154 may be flush with the surface of the array body 104. Optionally, the top surface 156 of the electrode(s) 154 may extend beyond the surface of the array body 104.

In one embodiment, the material used to form the carrier 132 and the biocompatible material 148 are the same material. For example, both the carrier 132 and the biocompatible material 148 could be silicone rubber. Alternatively, the material used to form the carrier 132 and the biocompatible material 148 may be different. Preferably, the biocompatible material 148 is capable of attaching to the carrier material without an additional adhesive. However, in some instances the carrier 132 material may be covered by an adhesive prior to adding the biocompatible material 148.

In at least some embodiments, the materials used to form the carrier 132 and the biocompatible material 148 have different properties. For example, the carrier 132 material and the biocompatible material 148 may have a different durometer, hardness, flexibility, rigidity, density, elasticity, etc. In one embodiment, the carrier 132 material and the biocompatible material 148 are the same material, but have different properties. For example, both the carrier 132 material and the biocompatible material 148 can be made of silicone rubber, but the silicone rubber used to form the carrier 132 material has a different durometer (e.g., a higher durometer) from the silicone rubber that is the biocompatible material 148.

Figure 11:
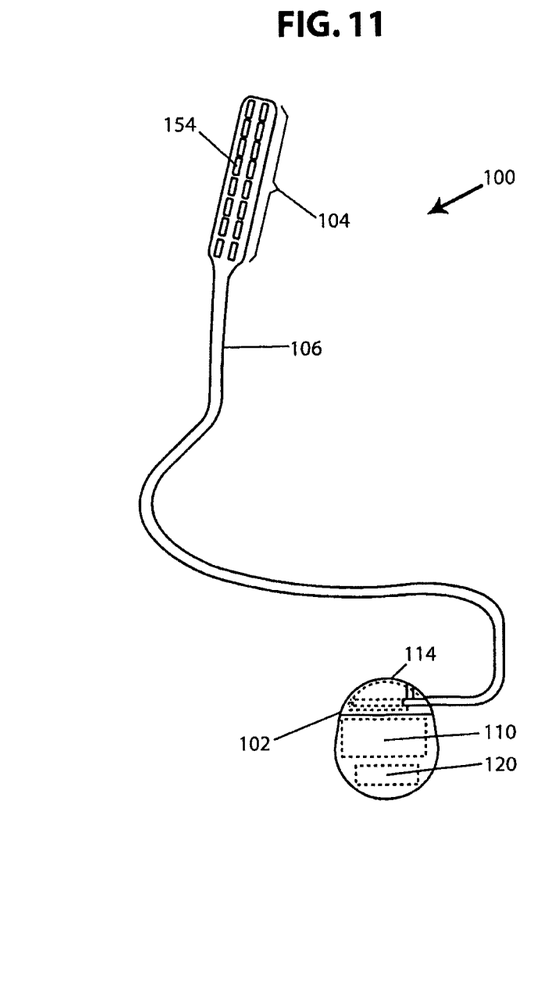
FIG. 11 is a schematic exterior perspective view of one embodiment of a stimulator system, according to the invention.

FIG. 11 illustrates schematically one embodiment of a stimulation system 100. The stimulation system includes a control module (e.g., a stimulator or pulse generator) 102, an array body 104, and at least one lead body 106 coupling the control module to the electrode array. The array body 104 and the lead body 106 form a lead. It will be understood that the system for stimulation can include more, fewer, or different components and can have a variety of different configurations including those configurations disclosed in the stimulator references cited herein. The formation of the array body 104 with the array of electrodes 154, carrier 132, and biocompatible material 148 is described above. The stimulation system or components of the stimulation system, including one or more of the lead body 106, the array body 104 and the control module 102, may be implanted into the body.

The control module 102 typically includes a housing 114 with an electronic subassembly 110 and, in at least some embodiments, a power source 120 disposed within a chamber in the housing. Preferably, the housing is resistant to moisture penetration into the chamber containing the electronic subassembly and power source. In some embodiments, water may diffuse through the housing. Preferably, the diffused water is relatively pure, without substantial ionic content, as deionized water is relatively non-conductive.

The housing 114 may be made of any biocompatible material including, for example, glass, ceramics, metals, and polymers. In one embodiment, the housing 114 of the control module is formed of a plastic material that resists the transport of moisture into the interior of the housing and is sufficiently sturdy to protect the components on the interior of the housing from damage under expected usage conditions. Preferably, the material of the plastic housing is a hydrophobic polymer material. The housing 114 may include additives such as, for example, fillers, plasticizers, antioxidants, colorants, and the like. The thickness of the walls of the housing may also impact the moisture permeability of the housing. A minimum thickness needed to achieve a particular degree of resistance to moisture transport will often depend on the material selected for the housing, as well as any additives.

Optionally, the housing 114 can be covered, in full or in part, with a coating. The coating can be provided to improve or alter one or more properties of the housing 114 including, for example, biocompatibility, hydrophobicity, moisture permeability, leaching of material into or out of the housing, and the like. In one embodiment, a coating can be applied which contains a compound, such as, for example, a drug, prodrug, hormone, or other bioactive molecule, that can be released over time when the stimulator is implanted. (In another embodiment, the housing itself may include such a compound to be released over time after implantation.)

Figure 12:
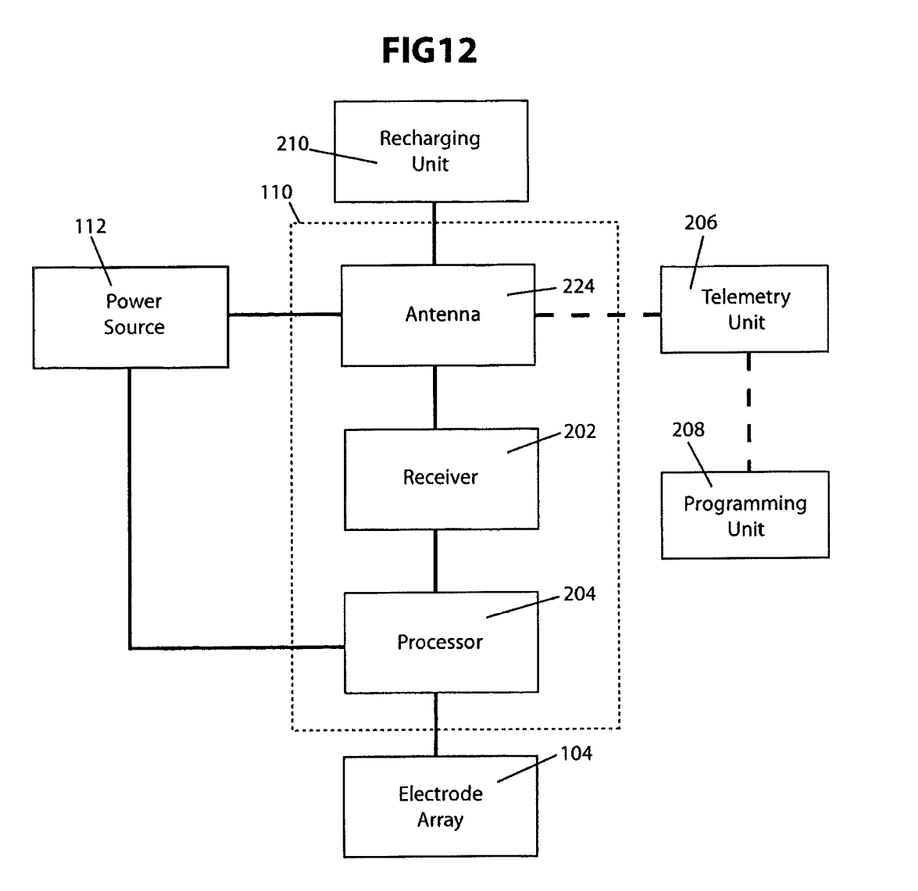
FIG. 12 is a schematic overview of components of a system for stimulation, according to an embodiment of the invention.

FIG. 12 is a schematic overview of one embodiment of components of a system for stimulation, including an electronic subassembly 110 (which may or may not include the power source 120), according to the invention. It will be understood that the system for stimulation and the electronic subassembly 110 can include more, fewer, or different components and can have a variety of different configurations including those configurations disclosed in the stimulator references cited herein. Some or all of the components of the system for stimulation can be positioned on one or more circuit boards or similar carriers within a housing of a stimulator, if desired.

Any power source 120 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 124 or a secondary antenna. The external power source can be in a device that is mounted on the skin of the user or in a unit that is provided near the stimulator user on a permanent or periodic basis.

If the power source 120 is a rechargeable battery, the battery may be recharged using the optional antenna 124, if desired. Power can be provided to the battery 120 for recharging by inductively coupling the battery through the antenna to a recharging unit 210 (see FIG. 12) external to the user. Examples of such arrangements can be found in the stimulator references identified above.

In one embodiment, electrical current is emitted by the electrodes 154 to stimulate motor nerve fibers, muscle fibers, or other body tissues near the stimulator. The electronic subassembly 110 provides the electronics used to operate the stimulator and generate the electrical pulses at the electrodes 154 to produce stimulation of the body tissues. FIG. 12 illustrates one embodiment of components of the electronic subassembly and associated units.

In the illustrated embodiment, a processor 204 is generally included in the electronic subassembly 110 to control the timing and electrical characteristics of the stimulator. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. In some embodiments with electrodes disposed on two or more sides of the housing, the processor may be used to identify which electrodes provide the most useful stimulation of the desired tissue. This process may be performed using an external programming unit, as described below, that is in communication with the processor 204.

Any processor can be used and can be as simple as an electronic device that produces pulses at a regular interval or the processor can be capable of receiving and interpreting instructions from an external programming unit 208 that allow modification of pulse characteristics. In the illustrated embodiment, the processor 204 is coupled to a receiver 202 which, in turn, is coupled to the optional antenna 124. This allows the processor to receive instructions from an external source to direct the pulse characteristics and the selection of electrodes, if desired.

In one embodiment, the antenna 124 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the stimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 124 and receiver 202 can be used to modify or otherwise direct the operation of the stimulator. For example, the signals may be used to modify the pulses of the stimulator such as modifying one or more of pulse duration, pulse frequency, pulse waveform, and pulse strength. The signals may also direct the stimulator to cease operation or to start operation or to start charging the battery. In other embodiments, the electronic subassembly 110 does not include an antenna 124 or receiver 202 and the processor operates as programmed.

Optionally, the stimulator may include a transmitter (not shown) coupled to the processor and antenna for transmitting signals back to the telemetry unit 206 or another unit capable of receiving the signals. For example, the stimulator may transmit signals indicating whether the stimulator is operating properly or not or indicating when the battery needs to be charged. The processor may also be capable of transmitting information about the pulse characteristics so that a user or clinician can determine or verify the characteristics.

The optional antenna 124 can have any form. In one embodiment, the antenna comprises a coiled wire that is wrapped at least partially around the electronic subassembly within or on the housing.

Any method of manufacture of the components of the system for stimulation can be used. For example, the power source and antenna can be manufactured as described in U.S. Patent Application Publication No. 2004/0059392. These components can then be placed inside the housing (or, alternatively, the housing can be formed, e.g., molded; around the components).

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of making a lead for a stimulation device, the method comprising:
 molding a carrier around an array of electrodes disposed in a pre-determined arrangement, wherein the array of electrodes comprises at least two rows of electrodes with at least one of the rows comprising a plurality of electrodes, wherein the carrier maintains the arrangement of the array of electrodes;
 attaching a plurality of conductors to the array of electrodes maintained by the carrier; and
 covering at least one surface of the carrier with a biocompatible material after coupling the plurality of conductors to the array of electrodes to form an insulating covering over connections between the conductors and the array of electrodes.

2. The method of claim 1, wherein molding the carrier comprises positioning the electrodes in a carrier mold, the method further comprising removing the carrier mold leaving the carrier and array of electrodes.

3. The method of claim 2, wherein the carrier mold comprises electrode positioning features.

4. The method of claim 3, wherein the electrode positioning features are depressions in the carrier mold.

5. The method of claim 3, wherein each of the electrodes comprises a front surface, a back surface, and a sidewall extending away from the back surface and defining a cavity bounded by the sidewall and the back surface, wherein the positioning features are protrusions in the carrier mold that fit within the cavities of the electrodes.

6. The method of claim 1, further comprising applying an adhesive to the conductors attached to the array of electrodes.

7. The method of claim 1, wherein covering at least one surface of the carrier with a biocompatible material comprises molding the biocompatible material over at least a portion of the carrier.

8. The method of claim 7, wherein molding the biocompatible material comprises positioning the carrier and electrodes in a mold.

9. The method of claim 7, wherein molding the biocompatible material comprises injection molding the biocompatible material.

10. The method of claim 1, wherein a material of the carrier and the biocompatible material area same material.

11. The method of claim 10, wherein the carrier and the biocompatible material have a different durometer.

12. The method of claim 1, further comprising forming the electrodes in a planar array prior to molding the carrier around the array of electrodes.

13. The method of claim 1, wherein each of the electrodes comprises a front surface, a back surface, and a sidewall extending away from the back surface and defining a cavity bounded by the sidewall and the back surface.

14. The method of claim 13, wherein attaching a plurality of conductors to the array of electrodes comprises attaching different one of the conductors to the back surface of each of the electrodes.

15. The method of claim 13, wherein covering at least one surface of the carrier with a biocompatible material comprises filling the cavity of each of the electrodes with the biocompatible material.

16. The method of claim 13, wherein covering at least one surface of the carrier with a biocompatible material comprises covering the back surface and sidewall of each of the electrodes with the biocompatible material.

17. The method of claim 1, wherein each of the electrodes has a concave shape.

18. The method of claim 1, wherein each of the conductors is a conductor wire.

19. The method of claim 1, wherein molding the carrier comprises injection molding the carrier around the array of electrodes.

20. The method of claim 1, further comprising, after molding the carrier, cleaning at least one surface of at least one of the electrodes.

* * * * *